United States Patent [19]

Cohen et al.

[11] Patent Number: 4,820,160
[45] Date of Patent: Apr. 11, 1989

[54] METHOD OF PRODUCING AN ELEMENT FOR PERSONAL IDENTIFICATIONS

[75] Inventors: Marvin Cohen; Susanne C. Mancin, both of St. Louis, Mo.

[73] Assignee: Ident Corporation of America, Inc., Creve Coeur, Mo.

[21] Appl. No.: 936,597

[22] Filed: Dec. 1, 1986

[51] Int. Cl.⁴ ............................................. A61C 13/00
[52] U.S. Cl. ..................................................... 433/229
[58] Field of Search .................. 433/229, 203.1, 215, 433/226; 283/900, 76, 1 R, 901; 128/1 R; 264/17, 16, 19

[56] References Cited

U.S. PATENT DOCUMENTS

| Re. 30,594 | 4/1981 | Samis | 433/229 |
|---|---|---|---|
| 3,925,896 | 12/1975 | McDowell | 433/203.1 X |
| 3,949,233 | 4/1976 | Gluck | 250/555 |
| 3,952,438 | 4/1976 | Propst et al. | 40/300 |
| 4,208,795 | 6/1980 | Muhlenann et al. | 433/203 |
| 4,233,964 | 11/1980 | Jefferts et al. | 128/1 R |
| 4,239,261 | 12/1980 | Richardson | 283/21 |
| 4,439,154 | 3/1984 | Mayclin | 433/229 |
| 4,473,353 | 9/1984 | Greggs | 433/215 |
| 4,512,744 | 4/1985 | Michnick et al. | 433/229 |
| 4,557,693 | 12/1985 | Elggren | 433/229 |

Primary Examiner—Larry Jones
Attorney, Agent, or Firm—Rogers, Howell, Moore & Haferkamp

[57] ABSTRACT

A method of producing personal identifying indicia for attaching to a person's body involves preparing a photohalide indicia on a plastic film which is then cut and polished. The method is especially useful to produce photo microdots which may be bonded to a wearer's teeth or other part of the body. The polished edge of the microdot has a smooth enlarged toroidal shape and aids in encapsulating the microdot in a bonding agent to adhere the microdot to a tooth.

20 Claims, 1 Drawing Sheet

U.S. Patent   Apr. 11, 1989   4,820,160
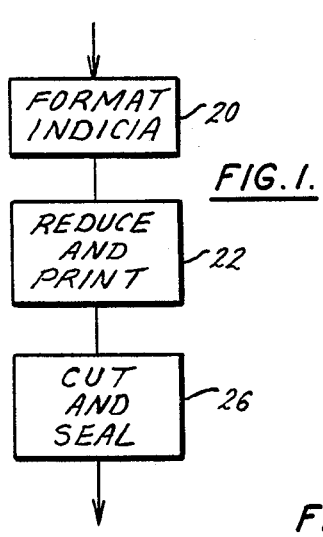
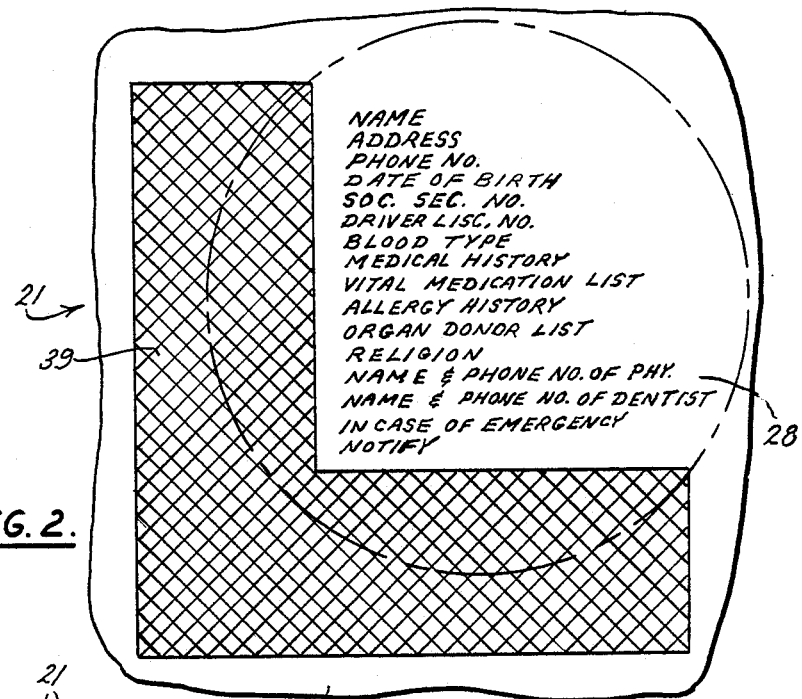
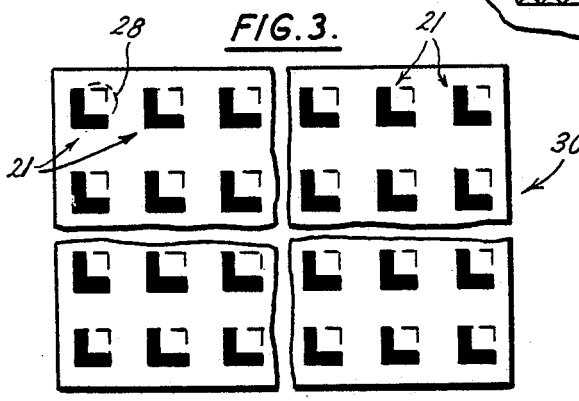
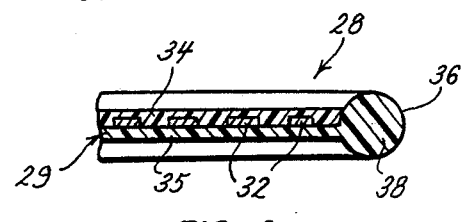
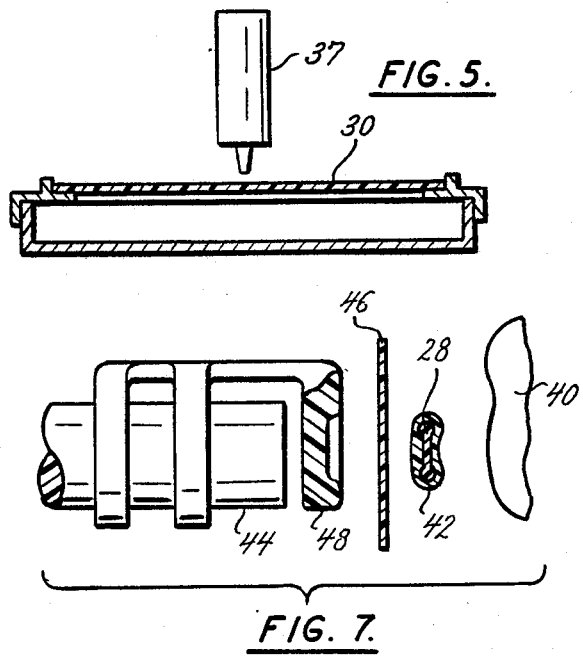

METHOD OF PRODUCING AN ELEMENT FOR PERSONAL IDENTIFICATIONS

BACKGROUND AND SUMMARY OF THE INVENTION

This invention relates to the method of providing specific personal indicia that can be bonded to an individual's anatomy.

Applicants are aware of the following patents: U.S. Pat. Nos. 3,952,438; 3,949,233; 4,027,391; 4,208,795; 4,233,964; 4,239,261; 4,473,353; 4,557,693; 4,439,154; 4,512,744 and U.S. Pat. No. Re. 30,594. The disclosures of the listed patents are incorporated by reference herein.

The need for positive identification of people, both living and deceased, has constantly plagued mankind. Some of the many vital needs for identification include criminal investigations and medical emergencies. Positive identification would especially benefit victims of accidents, amnesia, or other similar incapacities. Certain post mortem identification gives peace of mind and finality that sometimes does not exist with current methods in the wake of many tragic events.

Many previous positive identification systems require a complicated insertion process and may require complex electronic detection equipment to read the indicia. Some designs place indicia on or in dental prostheses or on implantable substrates that are difficult and costly to insert and remove and which involve complicated and intrusive procedures to read or retrieve.

The applicants have discovered a new method of preparing and installing personal identification indicia. Applicants' method involves taking personal identifying information and shrinking it onto a microdot through a photolithographic process, for example, using a silver halide process. This provides a simple, inexpensive method of reducing vast quantities of information. The indicia is developed on a substantially chemically inert thermoplastic film, such as a polyolefin. This gives long lasting durability and protection. The indicia is then cut and smoothed at the edges.

The finished microdot is bonded to an individual's anatomy, for example, to the teeth by any standard dental bonding agent. A particular advantage can be obtained by embedding the microdot in the adhesive to encapsulate, and further protect, the entire microdot.

The ease of application of the applicants' process is a major advantage over many current methods. This is because the microdot is smaller, thinner and lighter and because applicants' microdot is much less obtrusive. Applicants' microdot can be attached to any hard portion of an individual's body using common bonding agents. This results in less risk and fewer complications for the individual involved than many of the complicated intrusive processes that are currently used.

The applicants' process also provides for ease of information retrieval. Applicants' microdot may be read by visual observation by simple magnification; this represents a vast improvement over all previous methods, such as complicated extractions or the use of expensive, complex, electronic detection equipment.

The applicants' process of production is also very inexpensive. Not only are the materials that compose the microdot very inexpensive, but the operations are few and simple. The process lends itelf to mass production by permitting use of a high intensity light or laser cutting device to simultaneously cut and polish the microdot edge and create suitable edge characteristics. The viewing of the indicia can be done by simple magnification at the location where it is attached.

Applicants' system permits implementation of positive identification systems on a large scale. Large scale manual and automated information handling systems are possible. For example, by placing a large number of indicia on a single sheet of film, and using a device which cuts and polishes the indicia, a large quantity of indicia, i.e. many microdots, can be prepared in a short time. The applicants' process is vastly superior to any current method in this regard.

Applicants' process and product may be further understood by reference to the following drawings, Description of the Drawings, and Description of the Preferred Embodiments.

DESCRIPTION OF THE DRAWINGS

FIG. 1 is a flow chart of applicants' process.

FIG. 2 is a layout of the indicia prior to photographing.

FIG. 3 is an array of indicia on a film.

FIG. 4 is a side view of individual microdot after cutting and polishing.

FIG. 5 is a schematic of a device for cutting microdots.

FIG. 6 is a layout of the human mouth showing the microdot bonded to a tooth.

FIG. 7 is an exploded view showing a microdot and apparatus to attach the microdot to a tooth surface.

DESCRIPTION OF THE PREFERRED EMBODIMENTS

An overview of the entire process is flow charted in FIG. 1. The first step 20 shown is the preparation of the indicia (information), such as in the form 21, shown in FIG. 2. The information to be used and the shape of the indicia must be selected. The second step 22 is the reduction of the size and printing the indicia photographically, for example, using a two step process having a first reduction of 2.2X followed by a second reduction of 42X. A suitable device on which to reduce and print the information is a DOCUMATE II (TM), microfilm printer manufactured by Terminal Data Corporation. The DOCUMATE II uses a DMF-8 camera exposing images on 105 mm film using a moving film, fixed lens technique. Other equivalent reduction processes and equipment may be used. After printing, the indicia is cut and edge polished, at step 26, to form a complete microdot 28, as shown in FIG. 4. The reduced image is printed on archival quality laminated silver halide film 29, such as Eastman Kodak AHU-1460 (TM) 5 mil film, or equivalent. Preferably a suitable number of separate microdots 28 are printed in an array 30, such as shown in FIG. 3. As shown in FIG. 4, the microdot 28 is a multiple ply film 29 with the silver halide layer 32 between plies 34, 35. The support ply 35 is a suitable polymer film, such as a polyester. A 4 inch by 6 inch (10 cm×15 cm) print will hold a 13×25 array 30 of 325 microdots 28, each about 2 mm in effective diameter and having about 5 mm spacing center to center between adjacent microdots 28, as shown in FIG. 3. Typically a photographic quality within the parameters established for Class I microfiche is satisfactory for applicants' microdot 28. Generally, a grid pattern (array) 30 within the parameters set for Class I and Class II microfiche is satisfactory.

Individual microdots 28 may be cut from the array 30 by micro machining techniques. Applicants have found that the edges 36 of applicants' microdot 28 may be effectively cut and polished by a laser or high intensity light beam cutter 37. For example a Photon E505 (TM) 500 watt numerically controlled $CO_2$ laser, or a Mazak LASER-PATH (TM) 500 watt numerically controlled $CO_2$ laser or a comparable cutting machine can be used to cut applicants' microdot 28. The Photon E505 and the Mazak are conventional numerically controlled $CO_2$ laser cutting devices operating at a wave length of 10.6 microns. A laser cutting tool is shown schematically in FIG. 5. The beam is preferably collimated to have a taper of less than one degree and will produce a smoothness of cut of about 32 microinches. In cutting, the beam or cut width (kerf) is about 0.1 mm. The diameter of the cut microdot 28 is about 2 mm. The plies 34, 35 of the microdot 28 are fused and edge 36 is polished simultaneously with the cutting. Preferably, the heat creates a heat shrink and thickening of the polymer plies 34, 35 at the edge 36 of the microdot 28, producing a smooth thickened toroidal portion 38. This thickened portion 38 at edge 36 provides a particular advantage when bonding the microdot 28, as described herein. The power for the cut and heat shrink depends to a certain extent on the thickness of film 29 and the properties of the polymer of film 29, as well as on the particular cutting machine 37 used, but is typically about 80-100 watts for a typical photo film 29 having a thickness of about 0.25 mm. A cutting speed of about 10-50 m/min is normally satisfactory for film of this thickness. The beam is typically circular in cross section, but other beam shapes may be used. Fine tuning of the cut can easily be accomplished by adjusting the power level and by controlling the cut speed, as is known in the art.

As shown in FIG. 2, each completed microdot 28 has guide marks 39, formed when cutting the microdot 28 from the format 21. Guide marks 39 permit visual inspection to determine that the orientation of an installed microdot 28 is proper, without using magnification.

After the microdots 28 are cut, they are collected, either by hand or by an automated system, and packaged. Particular care should be taken to avoid contamination of the surface of microdot 28 with oil or dirt. If collection is by hand, for example, it is recommended that white gloves and other "clean room" type handling procedures be used in packaging and transporting finished microdots 28.

The finished microdot 28 is bonded to a hard body surface, for example, to a permanent tooth 40, as shown in FIGS. 6 and 7. Conventional dental adhesives of the self curing and light curing type, for example, may be used. DURAFIL (TM) acrylic dental bonding agent has been found to be satisfactory.

The device can be installed on the surface of a permanent tooth 40 by first pumacing the surface of the tooth 40, with flours of pumice and flushing the surface of the tooth with water. The prepared surface is then preferably etched, for example with 35% phosphorous acid liquid or gel for about 60 seconds and then again flushed copiously with water. The tooth 40 is then dried thoroughly and the microdot 28 is bonded to the prepared surface. Primary teeth may require a preliminary abrasion with an abrasive soft disc or dental stone to disrupt the prismatic outer layer of enamel, prior to pumacing.

Typically a discrete drop of an adhesive or bonding material 42, e.g., a conventional acrylic dental bonding agent, is placed on the prepared surface of the tooth 40. The microdot 28 is then placed into the center of the bonding material 42 using forceps or a wand 44, as described herein, the microdot 28 is oriented in proper relationship to the tooth 40 and pressed firmly to the tooth 40. A second drop of bonding material 42 is then placed over the microdot 28, insuring that adequate thickness is achieved over the outer surface and all edges of the microdot 28, to completely encapsulate the microdot 28 in the bonding material 42, as shown in FIG. 7.

Preferably a strippable form 46, such as a Mylar (TM) film, is placed over the microdot 28 and adhesive 42 to exclude air from the adhesive 42. If air is permitted to remain in contact with the adhesive 42 while it cures, the outer surface of the adhesive 42 often becomes clouded due to the formation of an air inhibited layer on the surface of the adhesive 42. The use of a strippable form 46 can prevent the formation of the air inhibited layer. On the other hand if the air inhibited layer is formed it may be removed by abrading away a thin layer from the upper surface of the adhesive 42, for example by using a standard fine dental buffing compound.

The use of a strippable form 46 also aids in maintaining a uniform thickness of bonding material 42 over the outer surface of the microdot 28 so that the microdot 28 is completely encapsulated in the adhesive 42. The presence of an acrylic layer completely over the microdot 28 provides a hard, transparent and uniform layer which protects the microdot 28 from scratching, as might occur normally from brushing the teeth. Scratching could interfere with reading the microdot 28. The hard polymer adhesive 42 forms a very hard, smooth and transparent layer which is resistant to scratching and which permits the microdot 28 to be read through the adhesive layer 42. If a form 46 is used, it may be transparent to UV light to permit activation of UV cured adhesives through the form 46. The form 46 may use a backing form 48, such as a shaped plastic, as shown in FIG. 7. Backing form 48 is preferably a transparent plastic, such as acrylic, which permits passage of activating light to initiate curing of light cured bonding agents. Wand 44 is an appliance which may be equipped with a conventional light source, not shown. The light source produces light of a wave length effective to initiate hardening of light cured agents, i.e., ultraviolet light. Once the microdot 28 and bonding agent 44 are in place the cure of the bonding agent can be initiated by activation of the light source. Backing form 48 may e mounted on wand 44 by clips, as shown.

The raised or toroidal edge 36 of the microdot 28 aids in bonding of the microdot 28 to the surface of the tooth 40, by providing additional surface to which the adhesive 42 can attach and by providing contact between the edge of the microdot 28 and the surface of the tooth 40 which permits even distribution of the bonding agent 42 under and around the microdot 28, as shown. It is advantageous to have contact between the edge of microdot 28 and the surface of tooth 40. This provides a smooth transition between the tooth 40 and the microdot 28 which permits an even coverage of the microdot 28 by the bonding agent 42. The smooth transition eliminates sharp edges which may not be fully covered by the bonding agent 42 due to surface tension effects. The surface of the raised toroidal edge 36 is preferably smoothly polished by the laser or light cutting process thus further reducing the effects of surface tension and assisting in producing a uniform coating of bonding agent 42 over the microdot 28. In addition, the raised outer edge 36 allows a film of adhesive 42 to be maintained over the information containing portion of the microdot 28, as shown in FIG. 7, thus protecting the microdot 28 from damage.

The bonded microdot 28 can easily be read, for example by 50X magnification. A variety of small magnifying periscopes, eye pieces, light guides and other devices may be used to view the microdot 28 without the necessity for removing the microdot 28 from the tooth 40 on which it is bonded. It will be appreciated that more complicated devices could be used, if desired, such as light pens, small video cameras or other devices that translate electronic images.

It will be appreciated by those skilled in the art that variations in the invention disclosed herein may be made without departing from the spirit of the invention. The invention is not to be limited to the specific embodiments disclosed herein, but only by the scope of the claims appended hereto.

We claim:

1. A method of producing a chip of specific personal indicia used for individual identification and the like comprising formating the indicia, reducing the size of the indicia and printing the reduced indicia on photosensitive film, cutting the printed indicia from the photosensitive film as a discrete identifying element and producing a raised edge on the element around substantially the entire perimeter thereof.

2. The method of claim 1 wherein the indicia is cut by a high intensity or laser light source.

3. The method of claim 2 wherein the cutting produces an enlarged smooth toroidal edge on the identifying element.

4. The method of claim 1 wherein the photosensitive film is a multiple ply film.

5. The method of claim 4 wherein the indicia is cut by a high intensity light or laser source.

6. The method of claim 5 wherein the cutting produces a heat polish of the polymer film.

7. The method of claim 5 wherein the cutting produces a heat polish of the plies of the polymer film and a heat shrunk raised toroidal edge on the element to aid in bonding of the chip.

8. The method of claim 1 wherein the photosensitive film is an archival quality polymer film.

9. The method of claim 8 wherein the film is a photohalide film.

10. The method of attaching a chip of specific personal indicia for individual identification to the tooth of an individual or other animal comprising bonding the chip to the tooth, the chip being a discrete element of photographic film having identifying indicia thereon, the chip further having a raised edge, the bonding step further comprising encapsulating the chip in a dental adhesive and bonding the dental adhesive to a tooth, the adhesive being applied over the surfaces of the chip including the raised edges to encapsulate the chip, the raised edge of the chip assisting the dental adhesive in substantially encapsulating the chip.

11. The method of claim 10 wherein the method includes placing a removable form over the chip and adhesive to exclude air from the adhesive during the curing, curing the adhesive and removing the form from the cured adhesive.

12. The method of claim 11 wherein the removable form is transparent to ultraviolet light.

13. The method of claim 11 wherein the adhesive is cured by ultraviolet light transmitted through the form.

14. The method of claim 10 wherein the adhesive is cured by ultraviolet light.

15. The method of claim 10 wherein the chip has an enlarged smooth toroidal edge.

16. A chip of specific personal indicia for individual identification and the like comprising a thin polymer film having photographic indicia thereon specific to an individual, the chip being of a small dimension and thin to fit unobtrusively within the mouth of an individual when bonded to a tooth, the chip having a raised edge around substantially its entire perimeter at its periphery to aid in bonding the chip to the tooth of an individual.

17. The chip of claim 14 wherein the photographic indicia is a photohalide indicia.

18. The chip of claim 16 wherein the chip has an enlarged smooth toroidal edge.

19. The chip of claim 16 wherein the film is multiple ply.

20. The chip of claim 16 wherein said film is encapsulated in adhesive.

* * * * *